(12) United States Patent
Otts et al.

(10) Patent No.: US 10,449,037 B1
(45) Date of Patent: Oct. 22, 2019

(54) FLEXIBLE TRANSPARENT CONDUCTORS FOR ELECTROWETTING LENSES

(71) Applicant: VERILY LIFE SCIENCES LLC, Mountain View, CA (US)

(72) Inventors: Daniel B. Otts, Pleasanton, CA (US); Kristopher A. Lavery, Pleasanton, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 87 days.

(21) Appl. No.: 15/230,715

(22) Filed: Aug. 8, 2016

(51) Int. Cl.
| | |
|---|---|
| *A61F 2/16* | (2006.01) |
| *G02C 7/08* | (2006.01) |
| *A61F 2/48* | (2006.01) |

(52) U.S. Cl.
CPC ...... *A61F 2/1635* (2013.01); *A61F 2002/169* (2015.04); *A61F 2002/16905* (2015.04); *A61F 2002/482* (2013.01); *A61F 2002/484* (2013.01); *A61F 2250/0003* (2013.01); *A61F 2250/0043* (2013.01); *G02C 7/085* (2013.01)

(58) Field of Classification Search
CPC .................................................... G02C 7/085
See application file for complete search history.

(56) References Cited

U.S. PATENT DOCUMENTS

| | | | | |
|---|---|---|---|---|
| 5,684,637 A * | 11/1997 | Floyd | ...................... | G02B 3/14 359/666 |
| 7,499,223 B2 * | 3/2009 | Berge | ...................... | G02B 3/14 359/665 |
| 8,466,366 B2 | 6/2013 | Srinivas et al. | | |
| 8,906,088 B2 | 12/2014 | Pugh et al. | | |
| 2007/0133103 A1 * | 6/2007 | Stempel | ................... | G02B 3/14 359/666 |
| 2008/0030870 A1 * | 2/2008 | Bruno | ...................... | G02B 3/14 359/666 |
| 2010/0020285 A1 * | 1/2010 | Berge | ...................... | G02B 3/14 351/159.41 |
| 2012/0310339 A1 * | 12/2012 | Berge | ...................... | G02B 3/14 623/6.22 |
| 2013/0000952 A1 * | 1/2013 | Srinivas | ................... | H01B 1/02 174/126.1 |
| 2013/0229618 A1 * | 9/2013 | Otts | ........................ | G02B 3/14 351/159.68 |
| 2013/0245754 A1 | 9/2013 | Blum et al. | | |
| 2014/0002790 A1 | 1/2014 | Pugh et al. | | |

(Continued)

FOREIGN PATENT DOCUMENTS

| | | | | |
|---|---|---|---|---|
| WO | WO 2007107589 A1 * | 9/2007 | .......... | A61F 2/1616 |
| WO | WO 2012/137067 A2 | 10/2012 | | |

*Primary Examiner* — David H Willse
*Assistant Examiner* — Javier G Blanco
(74) *Attorney, Agent, or Firm* — Christensen O'Connor Johnson Kindness PLLC

(57) ABSTRACT

A flexible intraocular lens including a flexible, transparent conductor disposed on a sidewall is disclosed herein. An example flexible intraocular lens includes an annular body and a transparent and flexible conductor. The annular body having at least one inner surface, where the annular body is formed from a flexible biocompatible material amenable to implantation into an eye. The transparent and flexible conductor formed on the at least one inner surface, the transparent and flexible conductor being one of a conductive polymer or a conductive nanowire-based mesh.

6 Claims, 4 Drawing Sheets

(56) References Cited

U.S. PATENT DOCUMENTS

| | | | |
|---|---|---|---|
| 2014/0253870 A1* | 9/2014 | Jiang | G02B 3/14 351/159.05 |
| 2014/0343387 A1 | 11/2014 | Pugh et al. | |
| 2014/0368789 A1* | 12/2014 | Webb | G02B 3/14 351/159.68 |
| 2015/0359626 A1 | 12/2015 | Caffey et al. | |

* cited by examiner

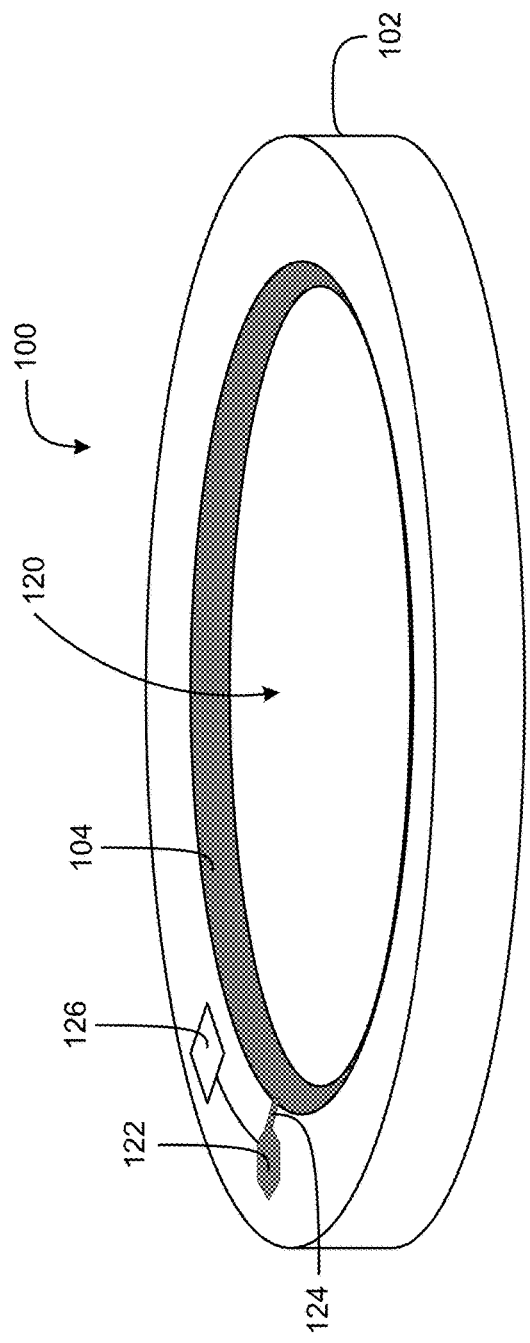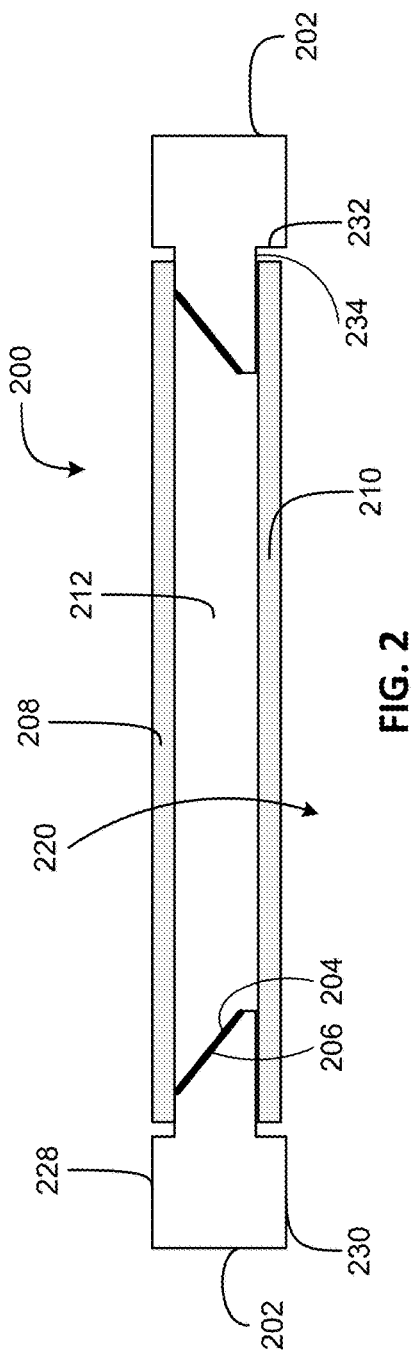

FLEXIBLE TRANSPARENT CONDUCTORS FOR ELECTROWETTING LENSES

TECHNICAL FIELD

This disclosure relates generally to intraocular lenses, and in particular but not exclusively, relates to flexible, transparent conductors for electrowetting lenses.

BACKGROUND INFORMATION

Presbyopia treatment may include implantation of a replacement lens. Such lenses, which may also be referred to as intraocular lenses, may provide static or dynamic accommodation, or a combination thereof. Various techniques may be available to provide dynamic accommodation, such as mechanical or electrical controlled accommodation. The accommodation may be provided by actuation of a dynamic optical component that provides multiple levels of optical power. The change in optical power may provide different focal distances to the user via the intraocular lens. The amount of actuation, however, may depend on the technique used, e.g., mechanical or electrical.

If electrical actuation is used, the electronics and conductors may need to meet certain requirements that relate to visibility, implantation compatibility, and the implantation procedures. For example, it may be desirable to have some or all of the electronics and/or conductors to be transparent and flexible, and further formed from materials amenable to implantation into an eye.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 1 is an illustration of an intraocular lens including a flexible, transparent conductive layer on an inner surface, in accordance with an embodiment of the disclosure.

FIG. 2 is a cross-sectional illustration of an intraocular lens including a flexible, transparent conductive layer on an inner surface, in accordance with an embodiment of the disclosure.

DETAILED DESCRIPTION

Figure 3:
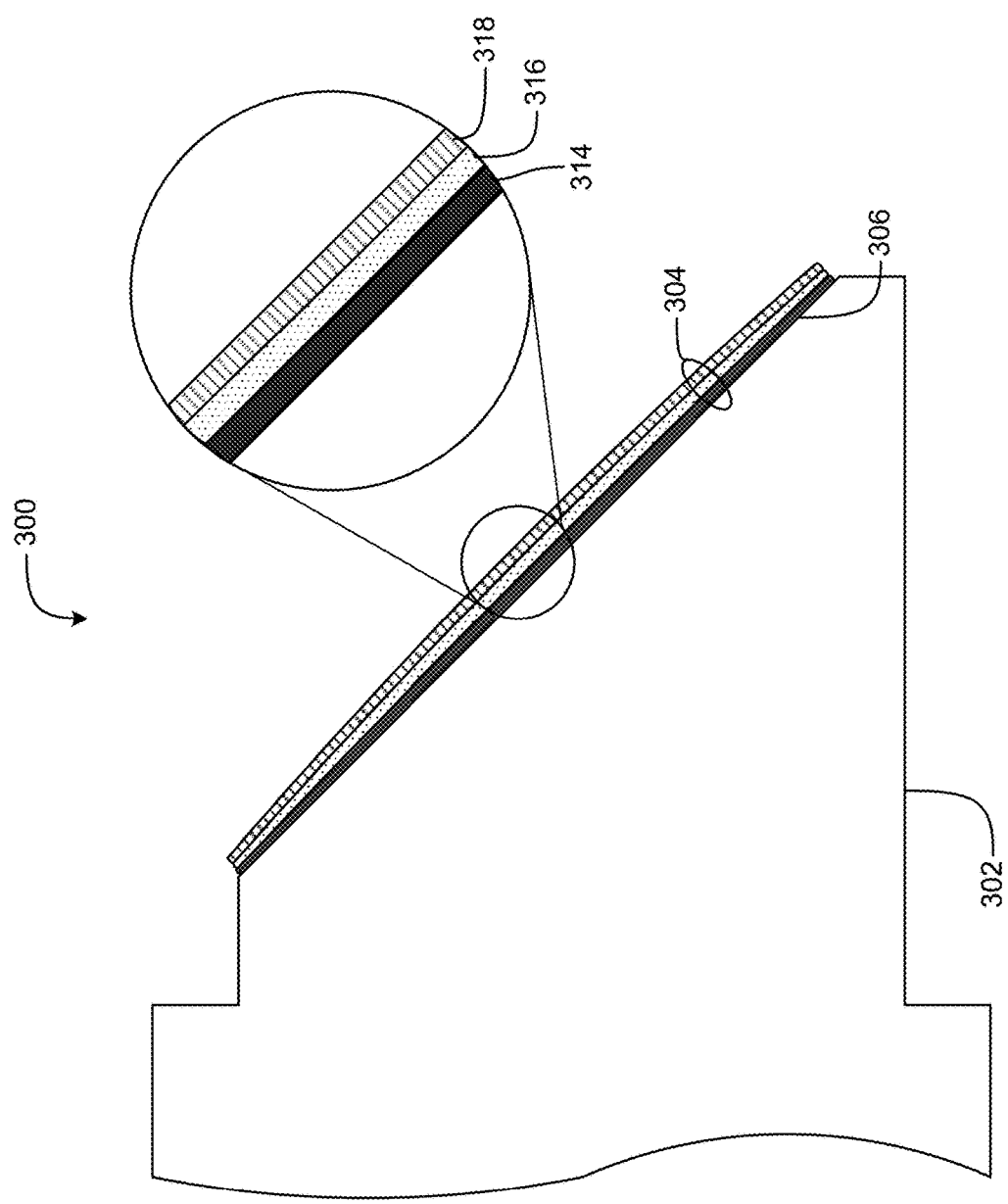
FIG. 3 is a cross-sectional illustration of an annular body of an intraocular lens having a flexible, transparent conductive layer formed thereon, in accordance with an embodiment of the disclosure.

Embodiments of an apparatus and method for a flexible, transparent conductor included in an intraocular lens are described herein. For example, the intraocular lens may have an internal cavity formed in an aperture of an annular body of the intraocular lens, where a surface of the center body that forms the aperture having the flexible, transparent conductor formed thereon. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An intraocular lens (IOL) may be implanted in a user's eye to assist in accommodation when the user's lens is no longer able to change focus as desired, for example. The IOL may have static optical power or may have the ability to dynamically accommodate, e.g., alter the optical power of the IOL, so the user may change focus similar to the natural eye. To provide dynamic accommodation, however, may require an IOL that is capable of changing the shape of an internal lens, which may provide the desired accommodation. While mechanical actuated accommodation may be an option, electrically actuated accommodation may be desired. Mechanical actuation may exhibit poor response and/or focal range. Electrically actuated lenses, however, may provide better range and response.

Electrically actuated lenses may require electrodes and interconnects within the IOL to provide the voltages, current, and power needed to drive the actuation. One actuation technique of interest is electrowetting. Electrowetting operates by changing surface energy of electrode dielectric coating on an electrode from hydrophobic to hydrophilic when bias is applied, and vice versa, for example. The change in surface energy may cause an interface between two immiscible liquids of different index of refraction to change shape, thereby providing a lensing effect. A voltage applied to the electrode may attract or repel one of the two immiscible liquids, which causes the change to the shape of the interface.

To implement the electrowetting, a conductor is needed to be in close proximity to the liquid affected by the change in electrostatic charge on the dielectric surface surface energy. If the technique is implemented in an IOL that will be implanted into an eye, the conductor may interfere with a user's vision if the conductor is opaque. As such, a transparent or semi-transparent conductor may be desirable.

Additionally, because the IOL will be implanted into the eye, a small incision in the eye may be desirable. Yet, because the IOL may be on the same size as the original lens, for example, a large incision may be required. However, if the IOL is capable of being rolled up into a cylinder shape or folded, a smaller incision may be possible. In general, most of the materials the IOL is formed from may be amenable to being rolled, but conventional conductors may experience reliability issues due to the stresses of rolling/flexing events. For example, conventional conductors may delaminate from a substrate and/or crack from the stresses induced from rolling. Accordingly, it may further be desirable for the transparent conductor to be flexible and deformable.

FIG. 1 is an illustration of an intraocular lens 100 including a flexible, transparent conductive layer on an inner surface in accordance with an embodiment of the disclosure. The illustrative embodiment of the intraocular lens (IOL) 100 includes an annular body 102, a conductive layer 104, a contact pad 106, an interconnect 108, and control electronics 126. In general, the IOL 100 may include other components, such as optical windows, and a dynamic optic which are not shown in FIG. 1. The IOL 100 may be formed from one or more biocompatible materials amenable to implantation into a user's eye. In some embodiments, the IOL 100 may be able to provide dynamic accommodation to a user based on electrowetting principles. For example, the IOL 100 may include two immiscible fluids, an oil and an electrolyte solution for example, that may provide dynamic accommodation by inducing a change in the shape of an interface between the two immiscible fluids in response to an applied voltage, which may provide a lensing behavior. In the illustrated embodiment of the IOL 100, the conductive layer 104 may provide a conductive layer for applying the voltage to induce the lensing behavior. The change in the interface shape may be due to the oil being attracted or repulsed by a surface energy of the conductive layer.

The annular body 102 may provide mechanical support for the various other features of the IOL 100. For example, the annular body 102 may be a substrate for such features discussed herein. In general, the annular body 102 may be formed from a biocompatible material that is amenable to implantation into an eye. Example materials may include silicones, sol-gels, and $^{AcrySof}$®. Other biocompatible materials, such as biocompatible hydrogel, silicone, hydrophobic acrylic, fluorinated polymethacrylate and/or the like, may also be used. The annular body may be a main structural component of the IOL 100 that provides a platform for other IOL 100 components. The annular body 102 may be flexibly capable of being rolled up and/or folded so that it may be manipulated into a smaller shape to accommodate insertion into an eye through a small incision, e.g., an incision roughly 2 mm in length.

In some embodiments, the annular body 102 may be a substrate for mounting various electronics, such as the control electronics 126. The control electronics 126 may be coupled to at least provide a voltage to the conductive layer 104. While the control electronics 126 is depicted as being mounted to a surface of the annular body 102, in some embodiments, the control electronics 126 may be tethered to the annular body 102 and coupled to the contact pad 122. In such an embodiment, the control electronics 126 may be mounted to a separate support structure, such as a substrate formed from a biocompatible material, and implanted in a different area of an eye than the IOL 100.

In the embodiment of the IOL 100, the annular body 102 is annulus-shaped, e.g., washer-shaped, having an opening 120, e.g., an aperture, formed there through. The opening 120 may provide an optical path for the IOL 100. In some embodiments, optical windows may be placed over the opening 120 on both a top and bottom surface of the center body 102 (see FIG. 2 for an example). While not shown in the IOL 100, the annular body 102 may include a recess along an inner edge of the annular body 102 to provide a location for mounting and centering one or more optical windows. The recess may provide an area to strengthen the mounting of the optical windows and provide a seal between the two.

The opening 120 may be formed by an inner surface, e.g., a sidewall, of the annular body 102. In the illustrated embodiment of the IOL 100, the sidewall includes the conductive layer 104 formed thereon. The sidewall may be at a non-orthogonal angle, e.g., oblique angle, to top and/or bottom surfaces of the annular body 102. For example, the sidewall may be at a 45° angle to at least one of the top or bottom surfaces of the annular body 102. In general, performance aspects of the IOL 100 may determine an oblique angle the sidewall may be at with respect to a top or bottom surface of the annular body 102, and other angles other than 45° are within the scope of the present disclosure. In some embodiments, the shape of the sidewall may form a conical frustrum.

The conductive layer 104 may be formed on the sidewall of the annular body 102. In some embodiments, it may be desirable that the conductive layer 104 be both flexible and at least semi-transparent. In general, the conductive layer 104 may be anywhere from 50% to 100% transparent. To obtain such qualities, the conductive layer 104 may be formed from materials that may be deformed, rolled up, or have a large degree of flexibility without negatively affecting their electrical and/or mechanical properties. Example materials may include conductive polymers, thin metal films, nanowire-based materials, and the like. In some embodiments, the conductive layer 104 may be a conductive nanowire-based mesh formed from a colloidal solution containing nanowires that upon processing may form the conductive nanowire-based mesh on the sidewall. In some embodiments, the conductive nanowire-based mesh may be a silver nanowire mesh, but other metal-based nanowires may also be used, such as aluminum, gold, copper, and the like.

In some embodiments, the conductive layer 104 may be encapsulated in one or more dielectrics. For example, a dielectric layer may be formed over at least the conductive layer 104 to provide durability, protection from other components, and mechanical support. The dielectric layer may be formed from a polymer, and it may desirable that the dielectric provide a conformal coating and be amenable to deposition on surfaces of various angles. An example polymer may be Parylene-C®, Parylene-N, Parylene-D, Parylene-HT, and Parylene-AF4. In some embodiments, the dielectric layer may be encapsulated in a surface energy changing layer, such as a fluoropolymer for example.

The contact pad 106 may be formed on a surface of the center body 102, such as a top surface or a bottom surface. In the illustrated embodiment of IOL 100, the contact pad 106 is shown on a top surface. The contact pad 106 may be formed from the same conductive material as is the conductive layer 104, else it may be formed from a different conductive material. The contact pad 106 may be coupled to the conductive layer 104 via the interconnect 108, which may also be formed from the same conductive materials forming the conductive layer 104. The contact pad 106 may provide a contact point for providing voltage to the conductive layer 104, for example.

In general, the conductive layer 104 may be energized with a voltage to induce electrowetting in the IOL 100, such as by the control electronics 126. The voltage on the conductive layer 104 may cause a change to the surface energy of the conductive layer 104 and/or one or more dielectric layers disposed on the conductive layer 104. The change in surface energy may cause the surface to change from hydrophilic to hydrophobic, or vice versa. The change in surface energy may cause one or more liquids in the aperture to change shape, which may affect an optical power of the IOL 100.

FIG. 2 is a cross-sectional illustration of an intraocular lens 200 including a flexible, transparent conductive layer on an inner surface in accordance with an embodiment of the disclosure. The intraocular lens (IOL) 200 may generally be similar to the IOL 100. The illustrated example of the IOL 200 is shown to include an annular body 202, a conductive layer 204, first and second optical windows 208 and 210, and two or more immiscible liquids 212. The IOL 200 may provide dynamic accommodation to a user induced by electrowetting principles.

The annular body 202 may be annulus-shaped and have an aperture 220 formed there through. A sidewall 206 of the center body 202 may at least partially form the aperture 220, along with other internal facets of the annular body 202. The center body 202 may provide structural support for the conductive layer 204, one or more contact pads (not shown) coupled to the conductive layer 204, and the optical windows 208, 210. Additionally, the center body 202 may provide a substrate for electronics and/or power sources for providing charge to at least the conductive layer 204 to induce the electrowetting-based dynamic accommodation of the IOL 200.

The annular body 202 may further have a recess formed on an inner edge on both the top and bottom surfaces 228, 230, respectively, that encircles the aperture 220. The recesses may provide a surface for mounting and sealing the optical windows 208, 210 to the annular body 202. The recess may be defined by surfaces 232 and 234 formed into the top surface 228, which may be mirrored on the bottom surface 230. In some embodiments, the recess formed into the top surface 228 and the recess formed into the bottom surface 230 may be different and provide different surface areas of the annular body 202. Additionally, the sidewall 206, which extends from recessed top and bottom surfaces of the annular body 202 may be truncated at an innermost point that defines the smallest diameter of the aperture 220.

The annular body 202 may be formed from one or more biocompatible materials, such as silicone, sol-gels, polymers, and the like. For example, the annular body 202 may be formed from AcrySof produced by Alcon of Fort Worth, Tex. The biocompatible material may be amenable to implantation in an eye allowing the IOL 200 to be implanted into the eye of a user. Additionally, the annular body 202 may be transparent so not to affect a user's vision after implantation.

The first and second optical windows 208, 210 may be mounted to top and bottom sides of the annular body 202. While top and bottom are used herein to discuss the opposite sides of the annular body 202, for example, the top and bottom designations do not notate any directionality to the IOL 200 and are used merely as a reference with respect FIG. 2. The optical windows 208, 210 may be transparent and disposed to cover the aperture 220. The optical windows 208, 210 may be with or without optical power. In some embodiments, one or both of the optical windows may provide static optical power to the IOL 200, which may be affected by the electrowetting-based dynamic accommodation of the IOL 200. In some embodiments, the optical windows 208, 210 may not have any optical power. In either embodiment, the optical windows 208, 210 may be coupled to the annular body 202 to retain the two immiscible liquids 212 within a cavity. The cavity may be formed by the aperture 220 and the optical windows 208, 210, with the conductive layer 204 exposed to the cavity.

Additionally, one of the optical windows may also be conductive. For example, the optical window 208, which the inner surface 206 faces, may be conductive. A transparent conductor, such as indium tin oxide (ITO) may be deposited on the optical window 208, for example. Having the optical window 208 be conductive may allow a potential difference to be formed between the conductive layer 204 and the optical window 208, which may be used to apply the electrowetting-induced accommodation.

The conductive layer 204 may be formed from two or more layers of material and may include electrically conductive materials and one or more dielectric layers. In some embodiments, the conductive layer 204 may include an electrically conductive layer in intimate contact with the sidewall 206, and one or more dielectric layers covering the conductive layer 204. For example, a silver nanowire mesh layer may form the conductive layer 204 and a polymer-based dielectric may conformally-coat the silver nanowire mesh layer. In some examples, there may be two polymer-based conformal layers encapsulating the silver nanowire mesh layer. In embodiments having two polymer-based dielectric layers, the dielectric layer in contact with the electrically conductive layer may provide durability, protection and mechanical support, whereas the second dielectric layer may provide an external surface having a different surface energy.

As shown in FIG. 2, the sidewall 206 of the annular body 202 is at a non-normal angle to top and bottom surfaces of the annular body 202. In some embodiments, the inner surface 206 is shaped like a conical frustrum. In some embodiments, the inner surface 206 is at 45° to top and bottom surfaces of the annular body 202.

In operation, charge may be provided to the conductive layer 204 by generating a potential difference between the conductive layer 204 and the optical window 208. The potential difference may cause charge to build up on the conductive layer 204, which may cause the surface energy of the conductive layer 204, or any encapsulating dielectric layers, to change. The change in surface energy may cause one of the fluids in the cavity to change shape in response. For example, a fluid may become more or less attracted to the conductive layer 204, which may cause an interface between the two immiscible fluids 212 to change. The change in their interface may cause a lensing effect, which may change an optical power of the IOL 200.

FIG. 3 is a cross-sectional illustration 300 of an annular body of an intraocular lens having a flexible, transparent conductive layer formed thereon in accordance with an embodiment of the disclosure. The annular body 302 may be an example of the annular body 102 and the annular body 202. In the illustrated embodiment of FIG. 3, the annular body 302 is shown to include the conductive layer 304 disposed on a sidewall 306.

The annular body 302 may be substantially similar to the annular body 202 and 102, in that it provides mechanical support for the conductive layer 304 and one or more optical windows (not shown). The annular body 302 may be formed from a transparent biocompatible material and may be used as an implantable intraocular lens, for example.

The conductive layer 304 may include three layers, such as an electrically conductive layer 314, a first dielectric layer 316, and a second dielectric layer 318. While the conductive layer 304 may be shown to include three layers, the inclusion of the three layers is shown as an example and any other number of layers is contemplated by the present disclosure. The conductive layer 304 may be an example of a conductive layer 104 and 204, and may be used to induce electrowetting-based dynamic accommodation in an intraocular lens, such as the IOL 100 or IOL 200.

The electrically conductive layer 314 may be a metallic layer or an electrically conductive polymer. In some embodiments, the electrically conductive layer 314 may be a silver nanowire mesh. For example, a silver nanowire mesh may be deposited using a colloidal solution containing silver nanowires. In some embodiments, the electrically conductive layer 314 may be coupled to a connection pad by an interconnect (see FIG. 4 for example).

The first dielectric layer 316 may encapsulate the electrically conductive layer 314. In some embodiments, the first dielectric layer 316 may form a conformal coating over the electrically conductive layer 314. In general, the first dielectric layer 316 may be a polymer-based dielectric that conformally-coats the electrically conductive layer 314, and further provides mechanical durability and mechanical support, and protection from chemicals to the electrically conductive layer 314. An example polymer-based dielectric may be Parylene-C, Parylene-N, Parylene-D, Parylene-HT, and Parylene-AF4. While the various Parylene-based polymers are disclosed as examples, any polymer-based dielectric that provides the mechanical support and chemical protection, as well as being flexible and deformable, is also contemplated by the present disclosure.

The second dielectric 318 may be optional, and may be included in the conductive layer 304 when it is desirable to alter the surface energy of the conductive layer 304. The second dielectric 318 may also be a polymer-based dielectric. For example, the second dielectric 318 may be a fluoropolymer, such as Teflon AF 1600. As noted, the second dielectric 318 may provide a different surface energy than the first dielectric layer 318, and may be included in the conductive layer 304 if the different surface energy is desired. For example, the one or more fluids 212 may determine whether the second dielectric 318 is to be included and may further determine what polymer to use for forming the second dielectric layer 318.

While the blowup of the interface between the inner surface 306 and the conductive layer 304 shows discrete layers, the physical relation of the layers may be different. For example, the electrically conductive layer 314 may have a rough morphology, which may be filled in and conformally-coated by the first dielectric layer 316.

Figure 4:
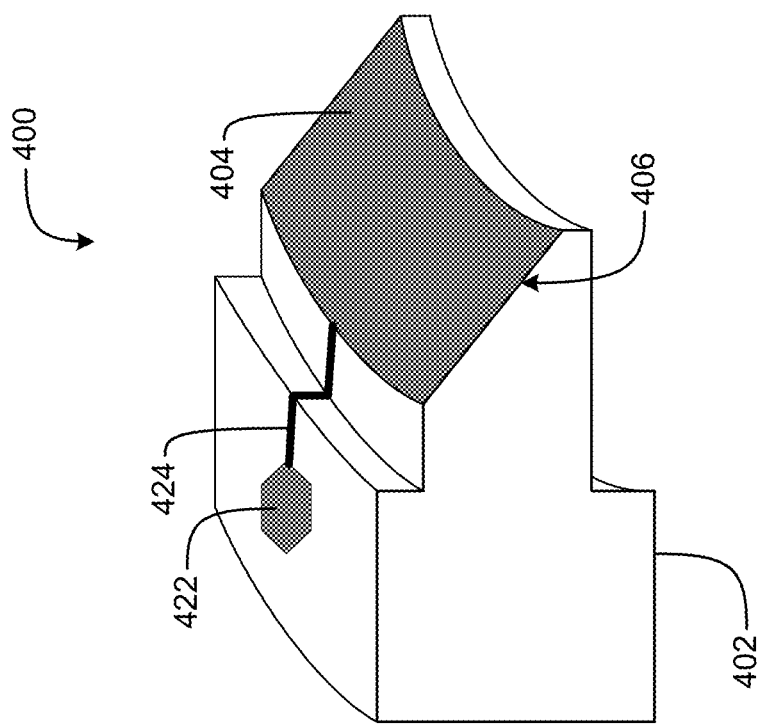
FIG. 4 is a cross-sectional illustration of an annular body of an intraocular lens having a flexible, transparent conductive layer, interconnect, and connection pad formed thereon, in accordance with an embodiment of the disclosure.

FIG. 4 is a perspective, cross-sectional illustration 400 of an annular body of an intraocular lens having a flexible, transparent conductive layer, interconnect, and connection pad formed thereon in accordance with an embodiment of the disclosure. The illustrated embodiment of FIG. 4 shows an annular body 402 including a conductive layer 404, a connection pad 422, and an interconnect 424. The annular body 402 may be an example of the annular body 102 and 202. The annular body 402 may be used as a component of an intraocular lens that provides electrowetting-based dynamic accommodation.

The annular body 402 includes a sidewall 406 having the conductive layer 404 formed thereon. The conductive layer 304 may be used for the conductive layer 404, for example. The conductive layer 404 may be coupled to contact pad 422 via the interconnect 424. Both the contact pad 422 and the interconnect 424 may be formed contemporaneously with the conductive layer 404, or, alternatively, at different times. The contact pad 422 may be formed on a top or bottom surface of the annular body 402, and may be used to coupled control electronics and/or a power source to the conductive layer 404.

Figure 5:
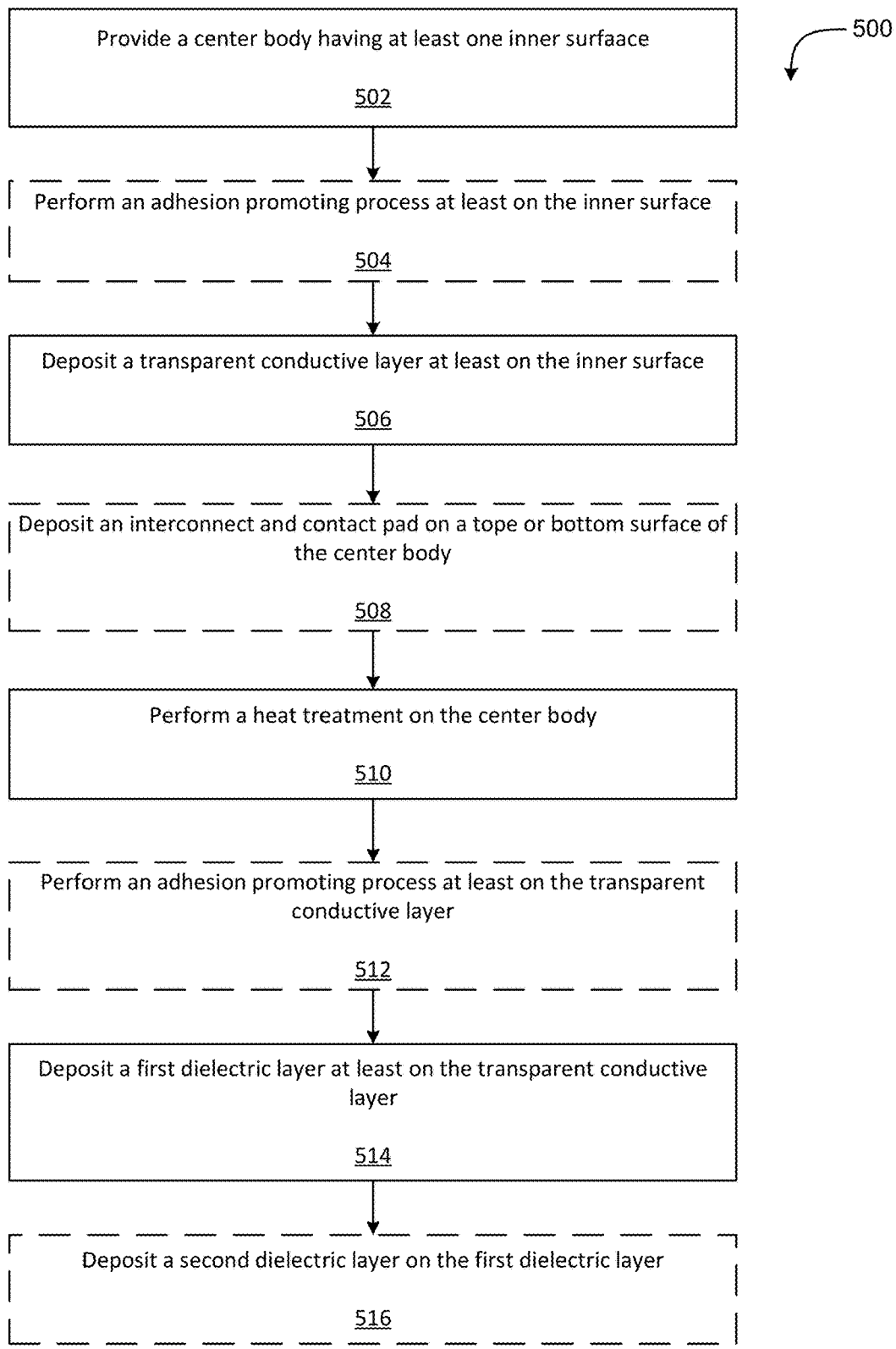
FIG. 5 is an example method of forming a flexible, transparent conductive layer on a surface of an intraocular lens, in accordance with an embodiment of the disclosure.

FIG. 5 is an example method 500 for forming a flexible, transparent conductive layer on an inner surface of an intraocular lens, in accordance with an embodiment of the disclosure. The method 500 may be used to form the conductive layers of FIGS. 1 through 4, and may also be used to form an optional contact pad and interconnect. The method 500 may also be an example process for forming at least a portion of an intraocular lens, such as the IOLs 100 and 200.

The method 500 may begin at step 502, which includes provide an annular body having at least one inner surface, e.g., sidewall, that forms an aperture through the annular body. The at least one inner surface may have a conical frustrum shape such that the inner surface is at an oblique or non-normal angle to top and bottom surfaces of the annular body. In some embodiments, the inner surface may be at 45° to the top and bottom surfaces. The annular bodies 102, 202, 302 and 402 may be an example of the annular body provided in step 502.

Step 502 may be followed by step 504, which includes performing an adhesion promoting process on the inner surface of the annular body. The adhesion promoting process may include a cleaning or surface treatment to alter a surface energy of the annular body, or it may include the deposition of a thin film of an adhesion promoting substance that may be cannibalized by a subsequent process step. In some embodiments, step 504 may be optional.

Step 504 may be followed by step 506, which includes deposit an electrically conductive layer at least on the inner surface of the annular body. In some embodiments, it may be desirable for the electrically conductive layer to be flexible and transparent. Based on the desirable characteristics of flexible and transparent, electrically conductive polymers or thin metal films may be deposited. For example, a silver nanowire mesh may be used for the electrically conductive layer.

The electrically conductive layer may be deposited using dip coating, ultrasonic spray coating, or jet dispensing techniques, among others. For example, a colloidal suspension including silver nanowires along with other components to provide a desired viscosity, evaporation rate, and surface tension along with one or more catalysts may be used to form a silver nanowire mesh on the inner surface of the annular body via dip coating, spray coating or jet dispensing. In some embodiments, the annular body may be masked such that only the inner surface is exposed during deposition of the electrically conductive layer. In some embodiments, the masking may include openings for an interconnect and a contact pad, which may both be deposited along with the electrically conductive layer and be formed from the same material.

Step 506 may be followed by step 508, which includes deposition of an interconnect and contact pad on a top or bottom surface of the annular body. Step 508, which may be optional, may be performed to provide an interconnect to the electrically conductive layer. As noted, step 508 may be optionally combined with step 506. Alternatively, step 508 may be broken into two steps—one of which may form the interconnect and the other of which may form the contact pad.

Step 508 may be followed by step 510, which includes perform a heat treatment on the annular body. The heat treatment may be carried out relatively low temperatures, around 125° C. for example, and may be performed to drive off solvents and binders in the electrically conductive layer. Additionally, the heat treatment may also promote stable conductivity by the electrically conductive layer.

Step 510 may be followed by step 512, which includes perform an adhesion promoting process at least on the transparent conductive layer. The adhesion promoting process may be similar to the process performed in step 504, for example. Step 512 may be an optional step of the method 500.

Step 512 may be followed by step 514, which may include deposit a first dielectric layer at least on the transparent conductive layer. The first dielectric may be a polymer-based dielectric and may be deposited using a vapor deposition technique. It may be desirable for the first dielectric to provide a conformal coat at least over the electrically conductive layer. Further, it may be desirable that the first dielectric be transparent and flexible while providing mechanical support at least to the electrically conductive layer, and to provide a chemical barrier to the electrically conductive layer. In some embodiments, the first dielectric may be formed from Parylene-C, and have a thickness of 0.5 to four microns. Other example dielectric materials may include Parylene-N, Parylene-D, Parylene-HT, Parylene-AF4, or any dielectric material known in the art that provides similar properties as discussed herein.

Step 514 may be followed by step 516, which may include deposition of a second dielectric layer. Between steps 514 and 516 an adhesion promoting process may be optionally performed. The second dielectric may be deposited to provide an outer surface having a different surface energy than the first dielectric layer may provide. The second dielectric may also be a polymer-based dielectric, and more specifically may be a fluoropolymer. In some embodiments, the second dielectric layer may be formed from Teflon AF 1600, and be about 20 to 200 nm in thickness. Step 516 may be optional for implementing the method 500.

The above steps of the method 500 may be preceded and followed by additional process steps that complete the formation of an IOL, such as the IOL 200. In some embodiments, the IOL that includes the electrically conductive layer and dielectric layers may be folded or rolled before implantation into an eye. As such, it may be desirable that the electrically conductive layer and dielectric layer or layers may be flexible enough to withstand the folding or rolling of the IOL before implantation. In some embodiments, the IOL may be rolled to a diameter small enough to fit through a two millimeter incision made in an eye.

The order in which some or all of the process blocks appear in method 500 should not be deemed limiting. Rather, one of ordinary skill in the art having the benefit of the present disclosure will understand that some of the process blocks may be executed in a variety of orders not illustrated, or even in parallel.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus, comprising:
   an annular body of an intraocular lens being annulus shaped, the annular body having a first external anterior side and a second external posterior side, a first recess formed on an inner edge on the first external anterior side, a second recess formed on an inner edge on the second external posterior side, and an inner surface encircling a central aperture through the annular body, wherein the inner surface is at an oblique angle to the first and second external sides of the annular body, wherein the inner surface is truncated forming a face defining a diameter of the central aperture, wherein the annular body is a monolithic member formed from a biocompatible material;
   a transparent flexible conductor disposed on the inner surface to electrically induce electrowetting in the intraocular lens, the transparent flexible conductor including a conductive silver nanowire material or a conductive polymer;
   a dielectric layer disposed over the transparent flexible conductor;
   a first optical window, being electrically conductive, disposed in the first recess in the first external anterior side and covering the central aperture, the first optical window electrically coupled for application of a potential difference between the first optical window and the transparent flexible conductor;
   a second optical window disposed in the second recess in the second external posterior side of the annular body and covering the central aperture; and
   two immiscible liquids disposed in a cavity defined by the annular body and the first and second optical windows, wherein the inner surface is exposed to the cavity, wherein the two immiscible liquids are contained in the cavity defined by the annular body and the first and second optical windows, and wherein a voltage applied to the transparent flexible conductor alters a wetting characteristic of the dielectric layer, thereby causing an interface between the two immiscible liquids to change an optical power of the intraocular lens,
   wherein the annular body is capable of reversible rolling or folding for insertion into an eye such that the annular body, when rolled or folded, has an outer diameter not exceeding 2 mm, and wherein the transparent flexible conductor and dielectric layer are capable of reversible rolling or folding while maintaining electrical conductivity and without delaminating from the inner surface having the oblique angle while the annular body is rolled or folded to have said outer diameter not exceeding 2 mm.

2. The apparatus of claim 1, further comprising a polymer layer disposed over the dielectric layer.

3. The apparatus of claim 1, wherein the dielectric layer is formed from one of Parylene-C, Parylene-N, Parylene-D, Parylene-HT, and Parylene-AF4.

4. The apparatus of claim 1 further comprising a contact pad, being electrically conductive, disposed on one of the first or second external sides of the annular body, wherein the transparent flexible conductor is electrically coupled to the contact pad via an interconnect.

5. The apparatus of claim 4, further comprising:
   an external electronic controller disposed in an insulating and biocompatible enclosure, being electrically coupled to the contact pad via a tether.

6. The apparatus of claim 1, wherein the first optical window comprises an electrically insulating substrate having a transparent flexible conducting film disposed thereon.

* * * * *